United States Patent [19]

Gayer et al.

[11] Patent Number: 6,150,374

[45] Date of Patent: *Nov. 21, 2000

[54] SUBSTITUTED CYCLOALKENES, PROCESS OF PREPARING THEM AND METHOD OF USING THEM AS PESTICIDES

[75] Inventors: Herbert Gayer, Monheim; Peter Gerdes, Aachen; Ralf Tiemann, Leverkusen; Stefan Dutzmann, Langenfeld; Klaus Stenzel, Düsseldorf, all of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/930,718

[22] PCT Filed: Mar. 25, 1996

[86] PCT No.: PCT/EP96/01309

§ 371 Date: Sep. 29, 1997

§ 102(e) Date: Sep. 29, 1997

[87] PCT Pub. No.: WO96/31463

PCT Pub. Date: Oct. 10, 1996

[30] Foreign Application Priority Data

Apr. 6, 1995 [DE] Germany .................. 195 12 886

[51] Int. Cl.$^7$ .................. A01N 37/50; A01N 43/54; C07C 251/48; C07D 239/52

[52] U.S. Cl. .................. 514/269; 514/361; 514/529; 514/530; 514/531; 514/538; 514/622; 514/676; 514/683; 514/684; 544/311; 548/130; 560/35; 560/60; 560/128; 564/163; 564/164; 564/165; 564/167; 564/256; 568/329; 568/330; 568/375; 568/377; 568/379

[58] Field of Search .................. 514/619, 640, 514/269, 361, 529, 530, 531, 538, 622, 676, 683, 684; 564/163, 256, 164, 165, 167; 544/311; 548/130; 560/35, 60, 128; 568/329, 330, 375, 377, 379

[56] References Cited

U.S. PATENT DOCUMENTS

Re. 33,989  7/1992  Wenderoth et al. .................. 514/522

5,189,063  2/1993  Klausener et al. .................. 514/530

FOREIGN PATENT DOCUMENTS

| 0 421 102 | 4/1991 | European Pat. Off. . |
| 0 468 684 | 1/1992 | European Pat. Off. . |
| 0 477 631 | 4/1992 | European Pat. Off. . |
| 0 582 925 | 2/1994 | European Pat. Off. . |
| 0 617 011 | 9/1994 | European Pat. Off. . |
| 27 05 881 | 8/1978 | Germany . |
| 40 12 792 | 10/1991 | Germany . |

OTHER PUBLICATIONS

Tetrahedron Lett. (1991), 2779–82, XP002010398, Kang, Han Young et al.

Chemical Abstracts, vol. 65, No. 13, Dec. 19, 1966, Abstract No. 19999h, J. Lubochinsky et al.

Helvetica Chimica Acta, Bd. 71, 1988, Basel CH, S.E. Denmark et al.

Journal of the Chemical Society, Perkin Transactions 1, Nr. 3, Mar. 1, 1986, 515–520, XP000567075, Brook G M et al.

J. AM. Chem. Soc. (1995), 117(43), 10635–44, XP002010399, Nakatani, Kazuhiko et al.

*Primary Examiner*—Richard L. Raymond
*Attorney, Agent, or Firm*—Norris, McLaughlin & Marcus, P.A.

[57] ABSTRACT

The invention relates to novel substituted cycloalkenes of the formula (I), (I)

to a plurality of processes for their preparation, and to novel intermediates and a plurality of processes for their preparation.

12 Claims, No Drawings

SUBSTITUTED CYCLOALKENES, PROCESS OF PREPARING THEM AND METHOD OF USING THEM AS PESTICIDES

This application is a 371 of PCT/EP96/01309, filed Mar. 25, 1996.

The invention relates to novel substituted cycloalkenes, to a plurality of processes for their preparation, and to novel intermediates and a plurality of processes for their preparation.

Certain substituted cycloalkenes are known to have fungicidal properties [cf. for example EP-A 421102].

However, in many cases the activity of these compounds is unsatisfactory.

This invention, accordingly, provides the novel substituted cycloalkenes of the general formula (I)

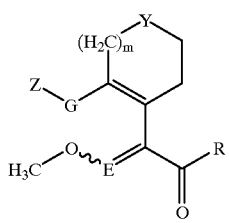

(I)

in which
  E represents methylidene or nitrogen,
  G represents a single bond, represents oxygen, sulphur, or represents respectively optionally halogen-, hydroxyl-, alkyl-, halogenoalkyl- or cycloalkyl-substituted alkanediyl or alkynediyl or one of the groupings below —Q—CQ—, —CQ—Q—, —CH$_2$—Q—, —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^1$)=N—O—, —C(R$^1$)=N—O—CH$_2$—, —N(R$^2$)—, —CQ—N(R$^2$)—, —N(R$^2$)—CQ—, —Q—CQ—N(R$^2$)—, —N=C(R$^1$)—Q—CH$_2$—, —N(R$^2$)—CQ—Q—, —CQ—N(R$^2$)—CQ—Q—, —N(R$^2$)—CQ—Q—CH$_2$—, —Q—C(R$^1$)=N—O—CH$_2$—, —N(R$^2$)—C(R$^1$)=N—O—CH$_2$—, —O—CH$_2$—C(R$^1$)=N—O—CH$_2$—, —N=N—C(R$^1$)=N—O—CH$_2$—, —T—Ar$^1$ or —T—Ar$^1$—Q—,
  where
    Ar$^1$ represents optionally substituted arylene, heteroarylene, cycloalkylene or heterocycloalkylene (i.e. an aliphatic ring which is doubly attached and in which one or more carbon atoms are replaced by hetero atoms, i.e. atoms other than carbon),
  n represents the number 0, 1 or 2,
  Q represents oxygen or sulphur,
  R$^1$ represents hydrogen, cyano or respectively optionally substituted alkyl, alkoxy, alkylthio, alkylamino, dialkylamino or cycloalkyl, and
  R$^2$ represents hydrogen, hydroxyl, cyano or respectively optionally substituted alkyl, alkoxy or cycloalkyl and
  T represents a single bond, represents oxygen, sulphur, —CH$_2$—O—, CH$_2$—S— or represents optionally substituted alkanediyl,
  m represents 0, 1 or 2,
  R represents alkyl, alkoxy, amino, hydroxylamino, alkoxyamino, alkylamino or dialkylamino.

Y represents methylene, oxygen, sulphur, or an optionally alkyl-substituted imino grouping ("azamethylene", NH, N-alkyl) and
  Z represents respectively optionally substituted alkyl, alkenyl, alkynl, cycloalkyl, aryl or heterocyclyl, where, if
    E represents nitrogen, G may also represent optionally halogen-, hydroxyl-, alkyl-, halogenoalkyl- or cycloalkyl-substituted alkenediyl or —CH$_2$—O—N=C(R$^1$)—.

Aryl represents aromatic, mono- or polycyclic hydrocarbon rings such as, for example, phenyl, naphthyl, anthranyl, phenanthryl, preferably phenyl or naphthyl, in particular phenyl.

Heterocyclyl represents saturated or unsaturated, and aromatic, compounds in the form of a ring in which at least one ring member is a hetero atom, i.e. an atom other than carbon. If the ring contains more than one hetero atom, these may be identical or different. Preferred hetero atoms are oxygen, nitrogen or sulphur. The compounds in the form of a ring may form a polycyclic ring system together with other carbocyclic or heterocyclic fused or bridged rings. Preference is given to mono- or bicyclic ring systems, in particular to mono- or bicyclic aromatic ring systems.

Furthermore, it was found that the novel substituted cycloalkenes of the general formula (I) are obtained when
a) keto compounds of the general formula (II)

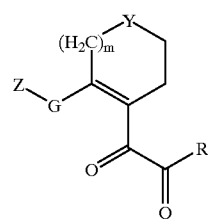

(II)

in which
  m, G, R, Y and Z are each as defined above
  are reacted with methoxyamine (O-methylhydroxylamine) or acid adducts thereof, or with a methoxymethyltriphenylphosphonium halide,
  if appropriate in the presence of an acid acceptor and if appropriate in the presence of a diluent,
where, if E represents nitrogen, it may in some cases be advantageous first to react the keto compounds of the general formula (II) with hydroxylamine or acid adducts thereof to give the corresponding oximes by the method of process a), and then to methylate these by conventional methods,
or
b) halogen compounds of the general formula (III)

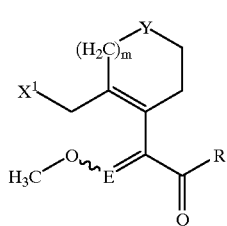

(III)

in which m, E, R and Y are each as defined above and $X^1$ represents halogen, preferably chlorine or bromine are reacted with a hydroxyl or mercapto compound of the general formula (IV), (V) or (VI)

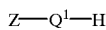
(IV)

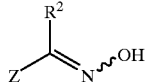
(V)

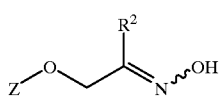
(VI)

in which $R^2$ and Z are each as defined above and $Q^1$ represents oxygen or sulphur, if appropriate in the presence of an acid acceptor and if appropriate in the presence of a diluent, or c) phosphorus compounds of the general formula (VII)

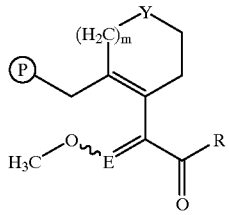
(VII)

in which m, R and Y are each as defined above,

E represents nitrogen,

Ⓟ represents $-P(R^3)_3{}^+X^-$ or represents $-PO(OR^4)_2$, $R^3$ represents aryl or alkyl, $R^4$ represents alkyl and X represents halogen are reacted with a keto compound of the general formula (VIII)

(VIII)

in which

Z is as defined above and $R^5$ represents hydrogen, alkyl or cycloalkyl, if appropriate in the presence of a diluent and if appropriate in the presence of an acid acceptor, or d) keto compounds of the general formula (IX)

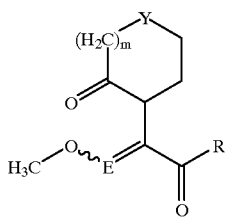
(IX)

in which

E, m, Y and R are each as defined above are reacted with halogen compounds of the general formula (X)

$$Z-A^1-X^2 \qquad (X)$$

in which $A^1$ represents a single bond, $-T-Ar^1-$ or $-CH_2-$ and

T, $Ar^1$ and Z are each as defined above and $X^2$ represents halogen or alkylsulphonyl, if appropriate in the presence of an acid acceptor and if appropriate in the presence of a diluent, or e) halogen compounds of the general formula (XI)

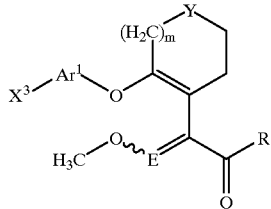
(XI)

in which m, $Ar^1$, E, R and Y are each as defined above and $X^3$ represents halogen or alkylsulphonyl are reacted with hydroxyl or mercapto compounds of the general formula (IV)

$$Z-Q^1-H \qquad (IV)$$

in which $Q^1$ and Z are each as defined above, if appropriate in the presence of an acid acceptor and if appropriate in the presence of a diluent, or f) esters of the general formula (XII)

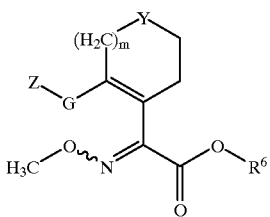

(XII)

in which
m, G, Y and Z are each as defined above and
$R^6$ represents alkyl are reacted with an amine of the general formula (XIII)

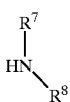

(XIII)

in which
$R^7$ represents hydrogen, hydroxyl or represents respectively optionally substituted alkyl or alkoxy and
$R^8$ represents hydrogen or represents optionally substituted alkyl, or an acid addition complex thereof,
if appropriate in the presence of an acid acceptor and if appropriate in the presence of a diluent
or g) amides of the general formula (XIV)

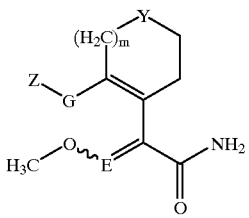

(XIV)

in which
E, G, m, Y and Z are each as defined above,
are reacted with an alkylating agent of the general formula (XIII)

$R^9$-$X^4$  (XIII)

in which
$R^9$ represents alkyl,
$X^4$ represents halogen or —O—$SO_2$—$R^{10}$ and
$R^{10}$ represents —O—$R^9$, alkyl or optionally substituted aryl,
if appropriate in the presence of a diluent and if appropriate in the presence of an acid acceptor.

Finally, it was found that the novel substituted cycloalkenes of the general formula (I) have very strong fungicidal action.

The compounds according to the invention, like the intermediates according to the invention, may be present as mixtures of different possible isomer forms, in particular of stereoisomers such as, for example, E- and Z-isomers, but also, if appropriate, of tautomers. The E- and the Z-isomers, any mixtures of these isomers, and the possible tautomeric forms are claimed.

The invention preferably provides compounds of the formula (I) in which

E represents methylidene or nitrogen,

G represents a single bond, represents oxygen, sulphur, or represents respectively optionally halogen-, hydroxyl-, $C_1$–$C_4$-alkyl-, $C_1$–$C_4$-halogenoalkyl- or $C_3$–$C_6$-cycloalkyl-substituted alkanediyl or alkynediyl having in each case up to 4 carbon atoms, or one of the groupings below —Q—CQ—, —CQ—Q—, —$CH_2$—Q—, —Q—$CH_2$—, —CQ—Q—$CH_2$—, —$CH_2$—Q—CQ—, —Q—CQ—$CH_2$—, —Q—CQ—Q—$CH_2$—, —N=N—, —S(O)$_n$—, —$CH_2$—S(O)$_n$—, —CQ—, —S(O)$_n$—$CH_2$—, —C($R^1$)=N—O—, —C($R^1$)=N—O—$CH_2$—, —N($R^2$)—, —CQ—N($R^2$)—, —N($R^2$)—CQ—, —Q—CQ—N($R^2$)—, —N=C($R^1$)—Q—$CH_2$—, —N($R^2$)—CQ—Q—, —CQ—N($R^2$)—CQ—Q—, —N($R^2$)—CQ—Q—$CH_2$—, —Q—C($R^1$)=N—O—$CH_2$—, —N($R^2$)—C($R^1$)=N—O—$CH_2$—, —O—$CH_2$—C($R^1$)=N—O—$CH_2$—, —N=N—C($R^1$)=N—O—$CH_2$—, —T—$Ar^1$ or —T—$Ar^1$—Q—,
where
n represents the numbers 0, 1 or 2,
Q represents oxygen or sulphur,
$R^1$ represents hydrogen, cyano, represents respectively optionally halogen-, cyano- or $C_1$–$C_4$-alkoxy-substituted alkyl, alkoxy, alkylthio, alkylamino or dialkylamino having in each case 1 to 6 carbon atoms in the alkyl groups or represents respectively optionally halogen-, cyano-, carboxyl-, $C_1$–$C_4$-alkyl- or $C_1$–$C_4$-alkoxy-carbonyl-substituted cycloalkyl having 3 to 6 carbon atoms, and
$R^2$represents hydrogen, hydroxyl, cyano or represents optionally halogen-, cyano- or $C_1$–$C_4$-alkoxy-substituted alkyl having 1 to 6 carbon atoms or represents optionally halogen-, cyano-, carboxyl-, $C_1$–$C_4$-alkyl- or $C_1$–$C_4$-alkoxy-carbonyl-substituted cycloalkyl having 3 to 6 carbon atoms and
$Ar^1$ represents phenylene, naphthylene or cycloalkylene, each of which is optionally mono- or polysubstituted by identical or different substituents, or represents heteroarylene or heterocycloalkylene having 3 to 7 ring members, at least one of which represent oxygen, sulphur or nitrogen and one or two more optionally represent nitrogen, the possible substituents preferably being selected from the list below:
halogen, cyano, nitro, amino, hydroxyl, formyl, carboxyl, carbamoyl, thiocarbamoyl;
respectively straight-chain or branched alkyl, alkoxy, alkylthio, alkylsulphinyl or alkylsulphonyl having in each case 1 to 6 carbon atoms;
respectively straight-chain or branched alkenyl or alkenyloxy having in each case 2 to 6 carbon atoms;
respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
respectively straight-chain or branched halogenoalkenyl or halogenoalkyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 6 carbon atoms in the individual alkyl moieties, and;

cycloalkyl having 3 to 6 carbon atoms and

T represents a single bond, represents oxygen, sulphur, —CH$_2$—O—, CH$_2$—S— or represents alkanediyl having 1 to 3 carbon atoms, m represents 0, 1 or 2, R represents alkyl, alkoxy, amino, alkylamino, hydroxylamino, alkoxyamino or dialkylamino having in each case 1 to 4 carbon atoms.

Y represents methylene, oxygen, sulphur, or an optionally alkyl-substituted imino grouping ("azamethylene", NH, N-alkyl) and Z represents alkyl having 1 to 8 carbon atoms which is optionally mono- or polysubstituted by identical or different substituents from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl (each of which may optionally be substituted by halogen);

represents respectively optionally halogen-substituted alkenyl or alkynyl having in each case up to 8 carbon atoms;

represents cycloalkyl having 3 to 6 carbon atoms which is in each case optionally mono- or polysubstituted by identical or different substituents from the group consisting of halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl and $C_1$–$C_4$-alkoxycarbonyl;

represents phenyl or naphthyl, each of which is optionally mono- or polysubstituted by identical or different substituents, or represents heterocyclyl having 3 to 7 ring members, at least one of which represents oxygen, sulphur or nitrogen and one or two more optionally represent nitrogen, the possible substituents preferably being selected from the list below:

halogen, cyano, nitro, amino, hydroxyl, formyl, carboxyl, carbamoyl, thiocarbamoyl;

respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 6 carbon atoms in the individual alkyl moieties;

alkylene or dioxyalkylene, each of which is doubly attached, each of which has 1 to 6 carbon atoms and each of which is optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

heterocyclyl or heterocyclyl-methyl having in each case 3 to 7 ring members, 1 to 3 of which are in each case identical or different hetero atoms—in particular nitrogen, oxygen and/or sulphur, where, if E represents nitrogen, G may also represent alkenediyl having 1 to 3 carbon atoms or —CH$_2$—O—N=C($R^1$)—.

In the definitions, the saturated or unsaturated hydrocarbon chains, such as alkyl, alkanediyl, alkenyl or alkynyl, are in each case straight-chain or branched, also in combination with hetero atoms, such as in alkoxy, alkylthio or alkylamino.

Halogen generally represents fluorine, chlorine, bromine or iodine, preferably fluorine, chlorine or bromine, in particular fluorine or chlorine.

The invention in particular provides compounds of the formula (I) in which

E represents methylidene or nitrogen,

G represents a single bond, represents oxygen, sulphur or represents respectively optionally fluorine-, chlorine-, bromine-, hydroxyl-, methyl-, ethyl-, n- or i-propyl-, trifluoromethyl-, cyclopropyl-, cyclobutyl-, cyclopentyl- or cyclohexyl-substituted methylene, dimethylene (ethane-1,2-diyl), ethyn-1,2-diyl or one of the groupings below —Q—CQ—, —CQ—Q—, —CH$_2$—Q—, —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C($R^1$)=N—O—, —C($R^1$)=N—O—CH$_2$—, —N($R^2$)—, —CQ—N($R^2$)—, —N($R^2$)—CQ—, —Q—CQ—N($R^2$)—, —N=C($R^1$)—Q—CH$_2$—, —N($R^2$)—CQ—Q—, —CQ—N($R^2$)—CQ—Q—, —N($R^2$)—CQ—Q—CH$_2$—, —Q—C($R^1$)=N—O—CH$_2$—, —N($R^2$)—C($R^1$)=N—O—CH$_2$—, —O—CH$_2$—C($R^1$)=N—O—CH$_2$—, —N=N—C($R^1$)=N—O—CH$_2$—, —T—Ar$^1$ or —T—Ar$^1$—Q—, where n represents the numbers 0, 1 or 2, Q represents oxygen or sulphur, $R^1$ represents hydrogen, cyano, represents respectively optionally fluorine-, chlorine-, cyano-, methoxy- or ethoxy-substituted methyl, ethyl, n- or i-propyl, n-, i- or s-butyl, methoxy, ethoxy, propoxy, butoxy, methylthio, ethylthio, propylthio, butylthio, methylamino, ethylamino, propylamino, dimethylamino or diethylamino or represents respectively optionally fluorine-, chlorine-, cyano-, carboxyl-, methyl-, ethyl-, n- or i-propyl-, methoxy-carbonyl- or ethoxy-carbonyl-substituted cyclopropyl, cyclobutyl, cyclopentyl or cyclohexyl, $R^2$ represents hydrogen, hydroxyl, cyano or represents respectively optionally fluorine-, chlorine-, cyano-, methoxy- or ethoxy-substituted methyl, ethyl, n- or i-propyl, n- or i-, s- or t-butyl or represents respectively optionally fluorine-, chlorine-, cyano-, carboxyl-, methyl-, ethyl-, n- or i-propyl-, methoxy-carbonyl- or ethoxy-carbonyl-substituted cyclopropyl, cyclobutyl, cyclopentyl or cyclohexyl, $Ar^1$ represents respectively optionally mono- to trisubstituted phenylene, naphthylene, furanediyl, thiophenediyl, oxazolediyl, isoxazolediyl, thiazolediyl, isothiazolediyl, 1,2,4-oxadiazolediyl, 1,3,4-oxadiazolediyl, 1,2,4-thiadiazolediyl, 1,3,4-thiadiazolediyl, pyridinediyl, pyrimidinediyl, pyridazinediyl, pyrazinediyl, 1,2,3-triazinediyl, 1,2,4-triazinediyl, 1,3,5-triazinediyl, oxiranediyl, oxetanediyl, tetrahydrofurandiyl, perhydropyrandiyl or pyrrolidinediyl, the possible substituents preferably being selected from the list below:

fluorine, chlorine, methyl, methoxy, methylthio, trifluoromethyl, difluoromethoxy, trifluoromethoxy, difluorochloromethoxy, or cyclopropyl and T represents a single bond, represents oxygen, sulphur, —CH$_2$—O—, CH$_2$—S—, methylene, ethylene or propylene, m represents 0 or 1, R represents methyl, ethyl, n- or i-propyl, methoxy, ethoxy, n- or i-propoxy, amino, methylamino, ethylamino, n- or i-propylamino, hydroxylamino, methoxyamino, dimethylamino, diethylamino.

Y represents methylene, oxygen, sulphur, —NH—, —N(CH$_3$)— or —N(C$_2$H$_5$)— and Z represents cyclopropyl, cyclobutyl, cyclopentyl or cyclohexyl, each of which is optionally mono- to hexasubstituted by fluorine, chlorine, bromine, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl, methoxy-carbonyl or ethoxy-carbonyl;

represents respectively optionally mono- to trisubstituted phenyl, naphthyl, furyl, thienyl, oxazolyl, isoxazolyl, thiazolyl, isothiazolyl, 1,2,4-oxadiazolyl, 1,3,4-oxadiazolyl, 1,2,4-thiadiazolyl, 1,3,4-thiadiazolyl, pyridinyl, pyrimidinyl, pyridazinyl, pyrazinyl, 1,2,3-triazinyl, 1,2,4-triazinyl, 1,3,5-triazinyl, oxiranyl, oxetanyl, tetrahydrofuryl, perhydropyranyl, pyrrolidinyl, piperidinyl or morpholinyl, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl;

trimethylene (propane-1,3-diyl), methylenedioxy or ethylenedioxy, each of which is doubly attached and each of which is optionally mono- or polysubstituted by identical or different substituents from the group consisting of fluorine, chlorine, methyl, trifluoromethyl, ethyl, n- and i-propyl, cyclopropyl, cyclobutyl, cyclopentyl or cyclohexyl, where, if E represents nitrogen, G may also represent ethene-1,2-diyl or —CH$_2$—O—N=C(R$^1$)—.

A particularly preferred group of compounds according to the invention is formed by those compounds of the formula (I)

in which

E represents methylidene or nitrogen,

G represents —O—CH$_2$—, or —CH$_2$—O— and m represents 0 or 1,

R represents methoxy, amino, methylamino or hydroxylamino,

Y represents methylene and

Z represents phenyl which is in each case mono- to trisubstituted by identical or different substituents, the possible substituents preferably being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoxyiminomethyl, ethoxyiminomethyl methoxyiminoethyl, ethoxyiminoethyl, methylenedioxy or ethylenedioxy, each of which is doubly attached and each of which is optionally mono- to tetrasubstituted by identical or different substituents from the group consisting of fluorine, chlorine, methyl, trifluoromethyl and ethyl, preferably fluorine.

A group of compounds according to the invention that is likewise particularly preferred is formed by those compounds of the formula (I)

in which

E represents methylidene or nitrogen,

G represents —C(R$^1$)=N—O—CH$_2$—, where

R$^1$ represents hydrogen, cyano, methyl, ethyl or cyclopropyl, m represents 0 or 1, R represents methoxy, amino, methylamino or hydroxylamino, Y represents methylene and Z represents phenyl, pyridyl or pyrimidinyl, each of which is optionally mono- to trisubstituted by identical or different substituents, the possible substituents preferably being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoxyiminomethyl, ethoxyiminomethyl methoxyiminoethyl, ethoxyiminoethyl, or methylenedioxy or ethylenedioxy, each of which is doubly attached and each of which is optionally mono to tetrasubstituted by identical or different substituents from the group consisting of fluorine, chlorine, methyl, trifluoromethyl or ethyl, preferably fluorine.

A group of compounds according to the invention that is furthermore particularly preferred is formed by those compounds of the formula (I)
in which E represents methylidene or nitrogen, G represents —T—Ar$^1$—Q—, where Q represents oxygen or nitrogen, Ar$^1$ represents 1,2,4-thiadiazolediyl, 1,3,4-thiadiazolediyl, 1,2,4-oxadiazolediyl, 1,3,4-oxadiazolediyl or represents pyridinediyl, pyrimidinediyl or 1,3,5-triazinediyl, each of which is optionally mono- or disubstituted by identical or different substituents from the group consisting of fluorine, chlorine, cyano, methyl, cyclopropyl, methoxy, methylthio, trifluoromethyl, difluoromethoxy, trifluoromethoxy and difluorochloromethoxy, T represents a single bond, represents oxygen, sulphur, —CH$_2$—O—, CH$_2$—S—, methylene, ethylene or propylene and m represents 0 or 1, R represents methoxy, amino, methylamino or hydroxylamino, Y represents methylene and Z represents phenyl, pyridyl or thienyl, each of which is optionally mono, to trisubstituted by identical or different substituents from the group consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy, difluorochloromethoxy, trifluoroethoxy, trifluoromethoxy or by methylenedioxy and ethylenedioxy, each of which is doubly attached and each of which is optionally mono- to tetrasubstituted by identical or different substituents from the group consisting of fluorine, chlorine, methyl, trifluoromethyl and ethyl, preferably fluorine.

Another particularly preferred group of compounds according to the invention is formed by those compounds of the formula (I)
in which E represents nitrogen, G represents ethene-1,2-diyl, m represents 0 or 1, R represents methoxy, amino, methylamino or hydroxylamino, Y represents methylene and Z represents phenyl, pyridyl or thienyl, each of which is optionally mono- to trisubstituted by identical or different substituents, the possible substituents preferably being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoxyiminomethyl, methoximinoethyl, ethoxyiminoethyl, methylenedioxy or ethylenedioxy, each of which is doubly attached and each of which is optionally mono- to tetrasubstituted by identical or different substituents from the group consisting of fluorine, chlorine, methyl, trifluoromethyl and ethyl, preferably fluorine.

The abovementioned general or preferred radical definitions apply both to the end products of the formula (I) and also, correspondingly, to the starting materials or intermediates required in each case for the preparation.

These radical definitions may be combined with one another as desired, i.e. combinations between the stated ranges of preferred compounds are also possible.

Examples of the compounds according to the invention are listed in Table 1:

TABLE I

Compounds of the formula (I) in which Z, G, m, Y, E and R are each as defined in the table.

| Z | G | m | Y | E | R |
|---|---|---|---|---|---|
| C$_6$H$_5$— | —CH=CH— | 0 | CH$_2$ | N | OCH$_3$ |
| C$_6$H$_5$— | —CH=CH— | 0 | CH$_2$ | N | NHCH$_3$ |
| C$_6$H$_5$— | —CH=CH— | 1 | CH$_2$ | N | OCH$_3$ |
| C$_6$H$_5$— | —CH=CH— | 1 | CH$_2$ | N | NHCH$_3$ |
| 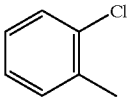 | 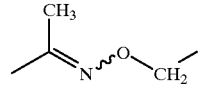 | 0 | CH$_2$ | N | NHCH$_3$ |

TABLE I-continued
Compounds of the formula (I) in which Z, G, m, Y, E and R are each as defined in the table.
| Z | G | m | Y | E | R |
|---|---|---|---|---|---|
| 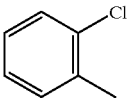 | 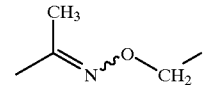 | 0 | CH$_2$ | CH | OCH$_3$ |
| 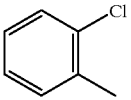 | 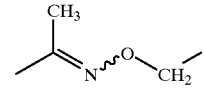 | 1 | CH$_2$ | N | OCH$_3$ |
| 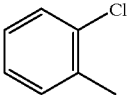 | 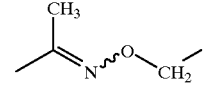 | 1 | CH$_2$ | N | NHCH$_3$ |
| 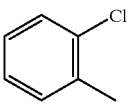 | 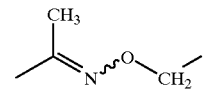 | 1 | CH$_2$ | CH | OCH$_3$ |
| 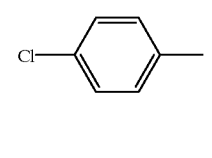 | 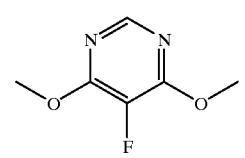 | 0 | CH$_2$ | N | OCH$_3$ |
| 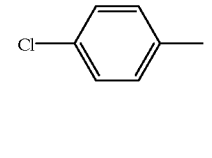 |  | 0 | CH$_2$ | N | NHCH$_3$ |
| 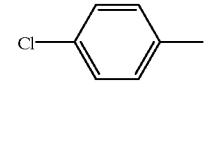 |  | 0 | CH$_2$ | CH | OCH$_3$ |
| 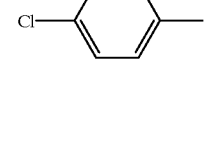 | 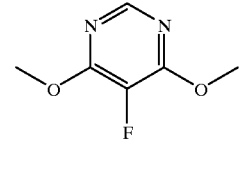 | 1 | CH$_2$ | N | OCH$_3$ |
| 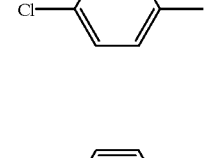 | 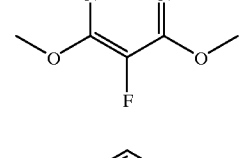 | 1 | CH$_2$ | N | NHCH$_3$ |
| 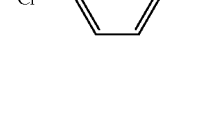 | 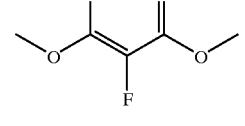 | 1 | CH$_2$ | CH | OCH$_3$ |

TABLE I-continued

Compounds of the formula (I) in which Z, G, m, Y, E and R are each as defined in the table.

| Z | G | m | Y | E | R |
|---|---|---|---|---|---|
| Cl—⟨phenyl⟩— | (methyl-thiadiazolyl-OMe) | 0 | CH$_2$ | N | OCH$_3$ |
| Cl—⟨phenyl⟩— | (methyl-thiadiazolyl-OMe) | 0 | CH$_2$ | N | NHCH$_3$ |
| Cl—⟨phenyl⟩— | (methyl-thiadiazolyl-OMe) | 0 | CH$_2$ | CH | OCH$_3$ |
| Cl—⟨phenyl⟩— | (methyl-thiadiazolyl-OMe) | 1 | CH$_2$ | N | OCH$_3$ |
| Cl—⟨phenyl⟩— | (methyl-thiadiazolyl-OMe) | 1 | CH$_2$ | N | NHCH$_3$ |
| Cl—⟨phenyl⟩— | (methyl-thiadiazolyl-OMe) | 1 | CH$_2$ | CH | OCH$_3$ |
| Cl—⟨phenyl⟩— | —O—CH$_2$— | 0 | —CH$_2$— | N | —OCH$_3$ |
| Cl—⟨phenyl⟩— | —O—CH$_2$— | 0 | —CH$_2$— | N | —NHCH$_3$ |
| Cl—⟨phenyl⟩— | —O—CH$_2$— | 0 | —CH$_2$— | CH | —OCH$_3$ |
| Cl—⟨phenyl⟩— | —O—CH$_2$— | 1 | —CH$_2$— | N | —OCH$_3$ |

Formula (II) provides a general definition of the keto compounds required as starting materials for carrying out the process a) according to the invention. In this formula (II), m, G, R, Y and Z each preferably or in particular have that meaning which has already been mentioned in connection with the description of the compounds of the formula (I) according to the invention as preferred or as particularly preferred for m, G, R, Y and Z.

Hitherto, the keto compounds of the formula (II) have not been known; as novel compounds, they form part of the subject matter of the present Application.

The keto compounds of the formula (II) are obtained (process a-1)) when organometallic compounds of the general formula (XVI)

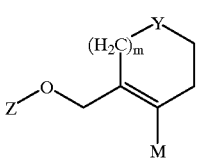

(XVI)

in which m, Y and Z are each as defined above and

M represents lithium or —Mg—X$^5$ where X$^5$ represents halogen are reacted with diethyl oxalate, dimethyl oxalate, ethyl oxalyl chloride or methyl oxalyl chloride, if appropriate in the presence of a diluent such as, for example, diethyl ether or tetrahydrofuran.

Formula (XVI) provides a general definition of the organometallic compounds required as starting materials for carrying out the process a-1) according to the invention. In this formula (XVI), m, Y and Z each preferably or in particular have that meaning which has already been mentioned in connection with the description of the compounds of the formula (I) according to the invention as preferred or as particularly preferred for m, Y and Z. M represents lithium or —Mg—$X^5$ where $X^5$ represents halogen, preferably bromine or iodine.

Hitherto, the organometallic compounds of the general formula (XVI) have not been known; as novel compounds, they form part of the subject matter of the present Application.

The organometallic compounds of the general formula (XVI) are obtained (process a-2)) when halogen compounds of the general formula (XVII)

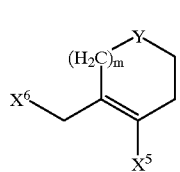

(XVIII)

in which m, $X^5$, Y and Z are each as defined above are reacted with magnesium turnings or butyllithium, if appropriate in the presence of a diluent such as, for example, diethyl ether or tetrahydrofuran, and if appropriate in the presence of a reaction auxiliary, such as, for example, tetramethylethylenediamine (TMEDA).

Formula (XVII) provides a general definition of the halogen compounds required as starting materials for carrying out the process a-2) according to the invention. In this formula (XVII), m, $X^5$, Y and Z each preferably or in particular have that meaning which has already been mentioned in connection with the description of the compounds of the formula (I) according to the invention, and of the organometallic compounds of the general formula (XVI) as preferred or as particularly preferred for m, $X^5$, Y and Z.

Hitherto, the halogen compounds of the general formula (XVII) have not been known; as novel compounds, they form part of the subject matter of the present Application.

The halogen compounds of the general formula (XVII) are obtained (process a-3)) when dihalogen compounds of the general formula (XVIII)

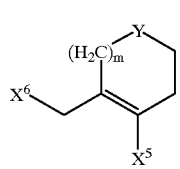

(XVIII)

in which m, $X^5$ and Y are each as defined above and $X^6$ represents halogen are reacted with hydroxyl or mercapto compounds of the general formula (IV)

Z—OH    (IV)

in which $Q^1$ and Z are each as defined above, if appropriate in the presence of a diluent such as, for example, acetonitrile or tetrahydrofuran, and if appropriate in the presence of an acid binder such as, for example, potassium t-butoxide.

Formula (XVIII) provides a general definition of the dihalogen compounds required as starting materials for carrying out the process a-3) according to the invention. In this formula (XVIII), m, $X^5$ and Y each preferably or in particular have the meaning which has already been mentioned in connection with the description of the compounds of the formula (I) according to the invention and of the organometallic compounds of the general formula (XVI) as preferred or as particularly preferred for m, $X^5$ and Y. $X^6$ represents halogen, preferably chlorine, bromine or iodine.

The dihalogen compounds of the general formula (XVIII) required as starting materials for carrying out the process a-3) according to the invention for preparing halogen compounds of the general formula (XVII) are known and/or can be prepared by methods known per se (cf. for example Tetrahedron. Letters (1988), 5789.

Formula (IV) provides a general definition of the hydroxyl or mercapto compounds also required as starting materials for carrying out the process a-3) according to the invention. In this formula (IV), $Q^1$ represents oxygen or sulphur. Z preferably or in particular has that meaning which has already been mentioned in connection with the description of the compounds of the formula (I) according to the invention as preferred or as particularly preferred for Z.

The hydroxyl or mercapto compounds of the general formula (IV) are known chemicals for synthesis.

Suitable diluents for carrying out the process a) according to the invention are all inert organic solvents. These preferably include aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide, sulphones, such as sulpholane, alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, their mixtures with water or pure water.

The process a) according to the invention is, if appropriate, carried out in the presence of a suitable acid acceptor. Suitable acid acceptors are all customary inorganic or organic bases. These include, for example, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process a) according to the invention, the reaction temperatures can be varied within a relatively wide range. In general, the process is carried out at temperatures between −20° C. and +140° C., preferably at temperatures between 0° C. and 100° C.

When carrying out the process a) according to the invention for preparing the compounds of the formula (I), generally 0.5 to 15 mol, preferably 0.5 to 5 mol, of methoxyamine or methoxymethyltriphenylphosphonium halide are employed per mole of the keto compound of the formula (II).

Formula (III) provides a general definition of the halogen compounds required as starting materials for carrying out process b) according to the invention. In this formula (III), m, E, R and Y each preferably or in particular have that meaning which has already been mentioned in connection with the description of the compounds of the formula (I) according to the invention as preferred or as particularly preferred for in, E, R and Y. $X^1$ represents halogen, preferably chlorine, bromine or iodine.

Hitherto, the halogen compounds of the formula (III) have not been known; as novel compounds, they form part of the subject matter of the present Application.

The halogen compounds of the formula (III) are obtained (process b-1)) when aryloxy compounds of the formula (XIX)

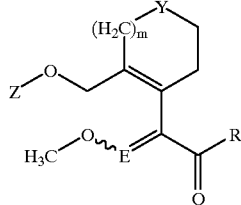

(XIX)

in which m, E, R, Y and Z are each as defined above are reacted with an ether-cleaving reagent such as, for example, boron tribromide or a hydrogen halide, if appropriate in the presence of a diluent such as, for example, acetic acid or toluene.

Formula (XIX) provides a general definition of the aryloxy compounds required as starting materials for carrying out the process b-1) according to the invention. In this formula (XIX), m, E, R, Y and Z each preferably or in particular have that meaning which has already been mentioned in connection with the description of the compounds of the formula (I) according to the invention as preferred or as particularly preferred for m, E, R, Y and Z.

The aryloxy compounds of the formula (XIX) are compounds according to the invention and can be prepared by the process a) according to the invention.

Formulae (IV), (V) or (VI) provide general definitions of the respective hydroxyl or mercapto compounds further required as starting materials for carrying out the process b) according to the invention. In these formulae (IV), (V) or (VI), $R^2$ and Z each preferably or in particular have that meaning which has already been mentioned in connection with the description of the compounds of the formula (I) according to the invention as preferred or as particularly preferred for $R^2$ and Z. $Q^1$ represents oxygen or sulphur.

The hydroxyl or mercapto compounds of the formulae (IV), (V) or (VI) are known chemicals for synthesis and/or can be prepared by methods known per se.

Suitable diluents for carrying out the process b) according to the invention are all inert organic solvents. These preferably include aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide, sulphones, such as sulpholane, alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, their mixtures with water or pure water.

The process b) according to the invention is, if appropriate, carried out in the presence of a suitable acid acceptor. Suitable acid acceptors are all customary inorganic or organic bases. These include, for example, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process b) according to the invention, the reaction temperatures can be varied within a relatively wide range. In general, the process is carried out at temperatures between −20° C. and +200° C., preferably at temperatures between 0° C. and 120° C.

When carrying out the process b) according to the invention for preparing the compounds of the formula (I), generally 0.5 to 15 mol, preferably 1 to 8 mol, of hydroxyl or mercapto compound of the formulae (IV), (V) or (VI) are employed per mole of the halogen compound of the formula (III).

Formula (VII) provides a general definition of the phosphorus compounds required as starting materials for carrying out the process c) according to the invention. In this formula (VII), m, E, R and Y each preferably or in particular have that meaning which has already been mentioned in connection with the description of the compounds of the formula (I) according to the invention as preferred or as particularly preferred for m, E, R and Y.

$\textcircled{P}$ represents —$P(R^3)_3{+}X{-}$ or —$PO(OR^4)_2$, where $R^3$ represents aryl, preferably phenyl, or $C_1$–$C_4$-alkyl, preferably butyl, and $R^4$ represents alkyl, preferably methyl or ethyl, and X represents halogen, preferably chlorine or bromine.

Hitherto, the phosphorus compounds of the formula (VII) have not been known; as novel compounds, they form part of the subject matter of the present Application.

The phosphorus compounds of the formula (VII) are obtained (process c-1a)) when nitrites of the general formula (XX)

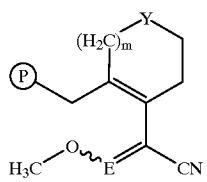

(XX)

in which m, $\textcircled{P}$, E and Y are each as defined above are reacted with water, if appropriate in the presence of an organic solvent, preferably an alcohol such as, for example, methanol or ethanol, or of a ketone such as, for example, acetone and if appropriate in the presence of a reaction auxiliary, such as, for example, acids or bases, preferably sodium carbonate or potassium carbonate, sodium hydroxide or potassium hydroxide or of the addition compound of urea and hydrogen peroxide, or of mixtures of reaction auxiliaries mentioned, at temperatures from −50° C. to 100° C., preferably from −20° C. to 50° C. (cf also the Preparation Examples).

The formula (XX) provides a general definition of the nitrites required as starting materials for carrying out the process c-1a) according to the invention for preparing the phosphorus compounds of the general formula (VII). In this formula (XX), $\textcircled{P}$, E, m and Y each preferably or in particular have that meaning which has already been mentioned in connection with the description of the compounds of the formula (I) according to the invention and of the phosphorus compounds of the formula (VII) as preferred or as particularly preferred for $\textcircled{P}$, E, m and Y.

Hitherto, the nitrites of the formula (XX) have not been known; as novel compounds, they form part of the subject matter of the present Application.

The nitrites of the formula (XX) are obtained (process c-2)) when oximes of the formula (XXI)

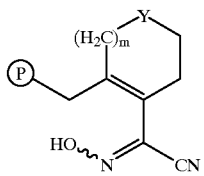

(XXI)

in which $\textcircled{P}$, m and Y are each as defined above are reacted with a methylating agent such as, for example, a methyl halide, sulphonate or carbonate, preferably dimethyl sulphate or iodomethane, if appropriate in the presence of a diluent such as, for example, an alcohol, ketone, amines, sulphones, amide or water or any mixtures thereof, preferably methanol or ethanol, and if appropriate in the presence of an acid acceptor, preferably an alkali metal hydroxide, carbonate or alkoxide such as, for example, sodium methoxide or ethoxide, at temperatures from −50° C. to 100° C., preferably from −20° C. to 50° C.

Hitherto, the oximes of the formula (XXI) have not been known; as novel compounds, they form part of the subject matter of the present Application.

The oximes of the formula (XXI) are obtained (process c-3)), when acetonitriles of the formula (XXII)

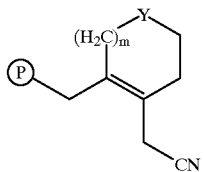

(XXII)

in which $\textcircled{P}$, m and Y are each as defined above, are reacted with an alkali metal nitrite such as, for example, sodium nitrite, or, preferably, an alkyl nitrite such as, for example, t-butyl nitrite or t-amyl nitrite, if appropriate in the presence of a diluent, preferably an alcohol such as, for example, methanol or ethanol, and if appropriate in the presence of an acid acceptor, preferably an alkali metal hydroxide, carbonate or alkoxide such as, for example, sodium methoxide or ethoxide, at temperatures from −50° C. to 100° C., preferably from −20° C. to 50° C.

In a preferred embodiment, the oximes of the formula (XXI) prepared by process c-3) are methylated directly, without work-up, by process c-2) to give the nitrites of the formula (XX) (cf. also the Preparation Examples).

Formula (XXII) provides a general definition of the acetonitriles required as starting materials for carrying out the process c-3) according to the invention for preparing the oximes of the general formula (XXI). In this formula (XXII), $\textcircled{P}$, m and Y each preferably or in particular have that meaning which has already been mentioned in connection with the description of the compounds of the formula (I) according to the invention, the phosphorus compounds of the formula (VII), the nitrites of the formula (XX), the oximes of the formula (XXI) and the acetonitriles of the formula (XXII) as preferred or as particularly preferred for $\textcircled{P}$, m and Y.

Hitherto, the acetonitriles of the formula (XXII) have not been known; as novel compounds, they form part of the subject matter of the present Application.

The acetonitriles of the formula (XXII) are obtained (process c-4)) when ketones of the formula (XXIII)

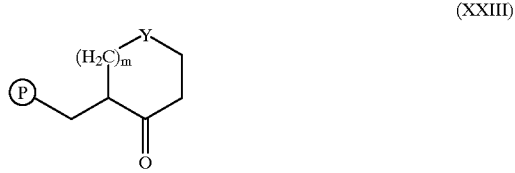

(XXIII)

in which
Ⓟ, m and Y are each as defined above are reacted with cyanoacetic acid,
if appropriate in the presence of a diluent such as, for example, toluene, and if appropriate in the presence of further reaction auxiliaries, preferably organic carboxylic acids such as, for example, acetic acid, and salts such as, for example, sodium acetate, or mixtures of the reaction auxiliaries mentioned, at temperatures from 0° C. to 200° C., preferably from 10° C. to 150° C. (cf. also the Preparation Examples).

The ketones of the formula (XXIII) required as starting materials for carrying out the process c-3) according to the invention for preparing the acetonitriles of the general formula (XXII) are known and/or can be prepared by processes known per se (cf. for example EP-A 453841).

The phosphorus compounds of the formula (VII) are also obtained (process c-1b)) when the halogen compounds of the general formula (III) described further above in connection with the process b) according to the invention for preparing the compounds of the formula (I) according to the invention are reacted with an ester of phosphorous acid, preferably the methyl or ethyl ester, or with a trialkylphosphine, preferably tributylphosphine, or with a triarylphosphine, preferably triphenylphosphine, if appropriate in the presence of a diluent, for example toluene or tetrahydrofuran, at temperatures from 0 to 120° C., preferably 0 to 80° C.

Formula (VIII) provides a general definition of the keto compounds further required as staring materials for carrying out the process c) according to the invention. In this formula (VIII), Z preferably or in particular has that meaning which has already been mentioned in connection with the description of the compounds of the formula (I) according to the invention as preferred or as particularly preferred for Z. $R^5$ represents hydrogen, alkyl or cycloalkyl, preferably hydrogen or methyl.

The keto compounds of the formula (VIII) are known chemicals for synthesis.

Suitable diluents for carrying out the process c) according to the invention are all inert organic solvents. These preferably include aliphatic, alicyclic or aromatic hydrocarbons such as, for example, petroleum ether, hexane, heptane, cyclohexane, methylcyclohexane, benzene, toluene, xylene or decal in; halogenated hydrocarbons such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide, sulphones, such as sulpholane, alcohols such as methanol, ethanol, n- or i-propanol, n-, i-, sec- or tert-butanol, ethanediol, propane-1,2-diol, ethoxyethanol, methoxyethanol, diethylene glycol monomethyl ether or diethylene glycol monoethyl ether.

The process c) according to the invention is, if appropriate, carried out in the presence of a suitable acid acceptor. Suitable acid acceptors are all customary inorganic or organic bases. These include, for example, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, preferably potassium tert-butoxide or sodium hydride, and tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process c) according to the invention, the reaction temperatures can be varied within a relatively wide range. In general, the process is carried out at temperatures between −50° C. and +100° C., preferably at temperatures between −20° C. and +50° C.

When carrying out the process c) according to the invention for preparing the compounds of the formula (I), generally 0.5 to 15 mol, preferably 0.8 to 5 mol, of the keto compound of the formula (VIII) are employed per mole of the phosphorus compound of the formula (VII).

Formula (IX) provides a general definition of the keto compounds required as starting materials for carrying out the process d) according to the invention for preparing the compounds of the formula (I) according to the invention. In this formula (IX), m, E, Y and R each preferably or in particular have that meaning which has already been mentioned in connection with the description of the compounds of the formula (I) according to the invention as preferred or as particularly preferred for m, E, Y and R.

Hitherto, the keto compounds of the formula (IX) have not been known; as novel compounds, they form part of the subject matter of the present Application.

The keto compounds of the formula (IX) are obtained (process d-1a)) when triketo compounds of the formula (XXIV)

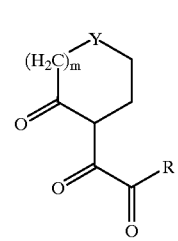

(XXIV)

in which
m, R and Y are each as defined above
are reacted with methoxyamine or acid adducts thereof, if appropriate in the presence of a diluent such as, for example, methanol, and if appropriate in the presence of a reaction auxiliary such as, for example, sodium acetate, at temperatures from 0 to 150° C., preferably 20 to 120° C.

Formula (XXIV) provides a general definition of the triketo compounds required as starting materials for carrying out the process d-1a) according to the invention for preparing the keto compounds of the formula (IX). In this formula (XXIV), m, R and Y each preferably or in particular have that meaning which has already been mentioned in connection with the description of the compounds of the formula (I) according to the invention as preferred or as particularly preferred for m, R and Y.

The triketo compounds of the formula (XXIV) are known and/or can be prepared by processes known per se (cf. for example J. Org. Chem. (1977), 42(7), 1180–5).

Formula (X) provides a general definition of the halogen compounds further required as starting materials for carrying out the process d) according to the invention for preparing the compounds of the formula (I) according to the invention. In this formula (X), $A^1$ represents —T—$Ar^1$— or —$CH_2$—. $Ar^1$, T and Z each preferably or in particular have that meaning which has already been mentioned in connection with the description of compounds of the formula (I) according to the invention as preferred or as particularly preferred for $Ar^1$, T and Z. $X^2$ represents halogen, preferably fluorine, chlorine, bromine or iodine, or represents alkylsulphonyl, preferably methylsulphonyl.

The halogen compounds of the formula (X) are mostly known chemicals for synthesis and/or can be prepared by processes known per se (cf. for example B. Khim.-Farm. Zh. (1989), 23(6), 705–7).

The novel halogen compounds of the formula (X), which also form part of the subject matter of the present invention, conform to the general formula (Xa)

(Xa)

in which $Q^1$ represents oxygen or sulphur and

Z is as defined above.

The halogen compounds of the general formula (Xa) are obtained (process d-1b)) when the hydroxyl or mercapto compounds of the general formula (IV), which have already been described further above, are reacted with 4,5,6-trifluoropyrimidine (DE-A 4137291), if appropriate in the presence of a diluent such as, for example, methanol, acetonitrile or tetrahydrofuran, and if appropriate in the presence of an acid binder such as, for example, sodium methoxide or potassium t-butoxide, at temperatures from 0 to 150° C., preferably 0 to 120° C.

Suitable diluents for carrying out the process d) according to the invention are all inert organic solvents. These preferably include aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide, sulphones, such as sulpholane, alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, their mixtures with water or pure water.

The process d) according to the invention is, if appropriate, carried out in the presence of a suitable acid acceptor. Suitable acid acceptors are all customary inorganic or organic bases. These include, for example, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process d) according to the invention, the reaction temperatures can be varied within a relatively wide range. In general, the process is carried out at temperatures between –20° C. and +150° C., preferably at temperatures between 0° C. and 100 C.

When carrying out the process d) according to the invention for preparing the compounds of the formula (I), generally 1 to 15 mol, preferably 1 to 8 mol, of the halogen compound of the formula (X) are employed per mole of the keto compound of the formula (IX).

Formula (XI) provides a general definition of the halogen compounds required as starting materials for carrying out the process e) according to the invention for preparing the compounds of the formula (I) according to the invention. In this formula (XI), m, $Ar^1$, E and Y each preferably or in particular have that meaning which has already been mentioned in connection with the description of the compounds of the formula (I) according to the invention as preferred or as particularly preferred for m, $Ar^1$, E and Y. $X^3$ represents halogen, preferably chlorine or fluorine, or represents alkylsulphonyl, preferably methylsulphonyl.

The halogen compounds of the formula (XI) are compounds according to the invention and can be prepared by process d) according to the invention.

Suitable diluents for carrying out the process e) according to the invention are all inert organic solvents. These preferably include aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide, sulphones, such as sulpholane, alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, their mixtures with water or pure water.

The process e) according to the invention is, if appropriate, carried out in the presence of a suitable acid acceptor. Suitable acid acceptors are all customary inorganic or organic bases. These include, for example, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process e) according to the invention, the reaction temperatures can be varied within a relatively wide range. In general, the process is carried out at temperatures between −20° C. and +1 50° C., preferably at temperatures between 0° C. and 100° C.

When carrying out the process e) according to the invention for preparing the compounds of the formula (I), generally 1 to 15 mol, preferably 1 to 8 mol, of the halogen compound of the formula (X) are employed per mole of the keto compound of the formula (IX).

Formula (XII) provides a general definition of the esters required as starting materials for carrying out the process f) according to the invention for preparing the compounds of the formula (I) according to the invention. In this formula (XII), m, G, Y and Z each preferably or in particular have that meaning that has already been mentioned in connection with the description of the compounds of the formula (I) according to the invention as preferred or as particularly preferred for m, G, Y and Z. $R^6$ represents alkyl, preferably methyl or ethyl.

The compounds of the formula (XII) are compounds according to the invention and can be obtained by the processes a) to e) according to the invention.

Formula (XIII) provides a general definition of the amines further required as starting materials for carrying out the process f) according to the invention. In this formula (XIII), $R^7$ represents hydrogen, alkyl, preferably having 1 to 4 carbon atoms, hydroxyl or alkoxy, preferably having 1 to 4 carbon atoms, in particular hydrogen, methyl, ethyl, n- or i-propyl, hydroxyl or methoxy, very particularly preferably hydrogen, methyl or hydroxyl. $R^8$ represents hydrogen or alkyl, preferably having 1 to 4 carbon atoms, in particular hydrogen, methyl or ethyl, very particularly preferably hydrogen.

The amines of the formula (XIII) are known chemicals for synthesis.

Suitable diluents for carrying out the process f) according to the invention are all inert organic solvents. These preferably include aliphatic, alicyclic or aromatic hydrocarbons such as, for example, petroleum ether, hexane, heptane, cyclohexane, methylcyclohexane, benzene, toluene, xylene or decalin, preferably toluene or xylene; halogenated hydrocarbons such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide, sulphones, such as sulpholane, alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, their mixtures with water or pure water.

The process f) according to the invention is, if appropriate, carried out in the presence of a suitable acid acceptor. Suitable acid acceptors are all customary inorganic or organic bases. These include, for example, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process f) according to the invention, the reaction temperatures can be varied within a relatively wide range. In general, the process is carried out at temperatures between −20° C. and +100° C., preferably at temperatures between 0° C. and 80° C.

When carrying out the process f) according to the invention for preparing the compounds of the formula (I), generally 1 to 100 mol, preferably 1 to 50 mol, of the amine of the formula (XIII) are employed per mole of the ester of the formula (XI).

The formula (XIV) provides a general definition of the amides required as starting materials for carrying out the process g) according to the invention. In this formula (XIV), m, E, G, Y and Z each preferably or in particular have that meaning which has already been mentioned in connection with the description of the compounds of the formula (I) according to the invention as preferred or as particularly preferred for m, E, G, Y and Z.

The compounds of the formula (XIV) are compounds according to the invention and can be obtained by the processes a) to f) according to the invention.

Formula (XV) provides a general definition of the alkylating agents further required as starting materials for carrying out the process g) according to the invention. In this formula (XV), $R^9$ represents alkyl, preferably methyl or ethyl, $X^4$ represents halogen, preferably chlorine, bromine or iodine, or $-O-SO_2-R^{10}$, where $R^{10}$ represents alkyl, preferably methyl, or represents optionally substituted aryl, preferably phenyl or tolyl, or represents $-O-R^9$.

The alkylating agents of the formula (XV) are known chemicals for synthesis.

Suitable diluents for carrying out the process g) according to the invention are all inert organic solvents. These preferably include aliphatic, alicyclic or aromatic hydrocarbons such as, for example, petroleum ether, hexane, heptane, cyclohexane, methylcyclohexane, benzene, toluene, xylene or decalin, preferably toluene or xylene; halogenated hydrocarbons such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide, sulphones, such as sulpholane, alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, their mixtures with water or pure water.

The process g) according to the invention is, if appropriate, carried out in the presence of a suitable acid acceptor. Suitable acid acceptors are all customary inorganic or organic bases. These include, for example, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process g) according to the invention, the reaction temperatures can be varied within a relatively wide range. In general, the process is carried out at temperatures between −20° C. and +200° C., preferably at temperatures between 0° C. and 100° C.

When carrying out the process g) according to the invention for preparing the compounds of the formula (I), generally 0.5 to 15 mol, preferably 0.8 to 5 mol, of the alkylating agent of the formula (XV) are employed per mole of the amide of the formula (XIV).

The processes a to g) according to the invention are generally carried out at atmospheric pressure. However, it is also possible to work at elevated or reduced pressure—in general between 0.1 bar and 10 bar.

The reactions are carried out and the reaction products are worked up and isolated according to known methods (cf. also the Preparation Examples).

The active compounds according to the invention have potent microbicidal activity and are employed in practice for controlling undesirable microorganisms. The active compounds are suitable for use as crop protection agents, in particular as fungicides.

Fungicides are employed in crop protection for controlling Plasmodiophoromycetes, Oomycetes, Chytridiomycetes, Zygomycetes, Ascomycetes, Basidiomycetes and Deuteromycetes.

Some pathogens causing fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *Peronospora brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *Pyrenophora graminea* (conidial form: Drechslera, synonym: Helminthosporium);

Cochliobolus species, such as, for example, *Cochliobolus sativus* (conidiae form: Drechslera, synonym: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;*

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling cereal diseases, for example against Erysiphe and Pseudocercosporella species, or diseases in viticulture, fruit-growing and vegetable-growing, for example against Plasmopara species.

Depending on their particular physical and/or chemical properties, the active compounds can be converted, if desired, to the customary formulations, such as solutions, emulsions, suspensions, powders, foams, pastes, granules, aerosols and microencapsulations in polymeric substances and in coating compositions for seeds, and ULV cold and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. In the case of the use of water as an extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water; liquefied gaseous extenders or carriers are to be understood as meaning liquids which are gaseous at ambient temperature and under atmospheric pressure, for example aerosol propellants such as halogenated hydrocarbons, or else butane, propane, nitrogen and carbon dioxide; suitable solid carriers are: for example, ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example, crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or, in their formulations, also as a mixture with known fungicides, bactericides, acaricides, nematicides or insecticides in order thus, for example, to widen the spectrum of action or to prevent development of resistance.

In many cases, synergistic effects are achieved.

Examples of co-components in mixtures are the following compounds:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)2-{2-[6-(2-cyanophenoxy)-pyrimidin-4-yloxy]phenyl}-3-methoxyacrylate; methyl (E)-methoxyimino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, fermizone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarinmol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

abamectin, abamectin, AC 303 630, acephate, acrinathrin, alanycarb, aldicarb, alphamethrin, amitraz, avermectin, AZ 60541, azadirachtin, azinphos A, azinphos M, azocyclotin,

*Bacillus thuringiensis,* bendiocarb, benfuracarb, bensultap, betacyluthrin, bifenthrin, BPMC, brofenprox, bromophos A, bufencarb, buprofezin, butocarboxin, butylpyridaben, cadusafos, carbaryl, carbofuran, carbophenothion, carbosulphan, cartap, CGA 157419, CGA 184699, chloethocarb, chlorethoxyfos, chloretoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lamda-cyhalothrin, lufenuron, malathion, mecarbam, mervinphos, mesulfenfos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamdon, phoxim, pirimicarb, pirimiphos M, primiphos A, profenofos, profenophos, promecarb, propaphos, propoxur, prothiofos, prothiophos, prothoate, pymetrozin, pyrachlophos, pyraclofos, pyraclophos, pyradaphenthion, pyresmethrin, pyrethrum, pyridaben, pyrimidifen, pyriproxifen, quinalphos,

RH 5992, salithion, sebufos, silafluofen, sulfotep, sulprofos, tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

It is also possible to mix the active compounds according to the invention with other known active compounds, such as herbicides, or else fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by wetting, spraying, atomizing, broadcasting, dusting, foaming, brushing on and the like. It is further possible to apply the active compounds by the ultra-low volume method or to inject the active compound formulation, or the active compound itself, into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the treatment site.

PREPARATION EXAMPLES

Example (1)

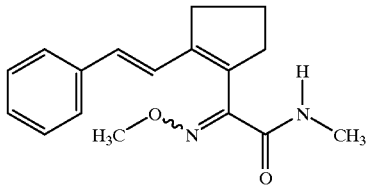

Process g)

3.6 g (0.013 mol) of 1-methoxyimino-1-[2-(2-phenyl-ethen-1-yl)-penten-1-yl]-acetamide in 15 ml of toluene are stirred with 1.12 g (≈0.017 mol) of powdered KOH and 5.84 g (0.041 mol) of methyl iodide at room temperature for 12 hours. Dilute hydrochloric acid is added, and the mixture is extracted with ethyl acetate. The organic phase is dried over sodium sulphate and concentrated under reduced pressure. The residue is chromatographed over silica gel using a mixture of ethyl acetate-cyclohexane (1:1). Recrystallization from methanol affords 0.5 g (13.2% of theory) of N-methyl-1-methoxyimino-1-[2-(2-phenyl-ethen-1-yl)-penten-1-yl]-acetamide of melting point 135–140° C.

Example (2)

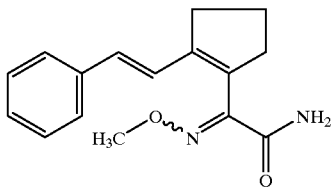

Process c)

9.44 g (0.03 mol) of 1-methoxyimino-1-(2-diethylphosphonomethyl-penten-1-yl)-acetamide and 3.2 g (0.03 mol) of benzaldehyde are dissolved in 30 ml of tetrahydrofuran and cooled to 0° C. At this temperature, a solution of 3.36 g (0.03 mol) of potassium tert-butoxide and 30 ml of tetrahydrofuran is added dropwise and the mixture is left standing at 20° C. for 12 hours. The mixture is then mixed with water and extracted with ethyl acetate. The organic phase is dried over sodium sulphate and concentrated under reduced pressure. The residue is chromatographed over silica gel using a mixture of ethyl acetate-cyclohexane (1:1). 1.3 g (16.2% of theory) of 1-methoxyimino-1-[2-(2-phenyl-ethen-1-yl)-penten-1-yl]-acetamidof melting point 155° C. are obtained.

Example (3)

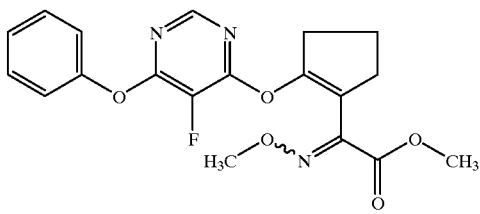

Process d)

2 g (0.007 mol) of 70% strength methyl 1-methoxyimino-1-(2-oxocyclopentan-1-yl)-acetate in 10 ml of dimethylformamide are stirred with 0.54 g (0.01 mol) of sodium methoxide (M=54.02) at room temperature for 15 minutes. 2.08 g (0.01 mol) of 5,6-difluoro-4-phenoxypyrimidine are added and the mixture is stirred at room temperature for 3 hours. The mixture is poured onto water and extracted with diethyl ether, and the organic phase is dried over sodium sulphate and concentrated under reduced pressure. The residue is recrystallized from methanol. 1.43 g (52.5% of theory) of methyl 1-methoxyimino-1-[2-(5-fluoro-6-phenoxy-pyrimid-4-yl)-penten-1-yl]-acetate of melting point 133–135° C. are obtained.

Example (4)

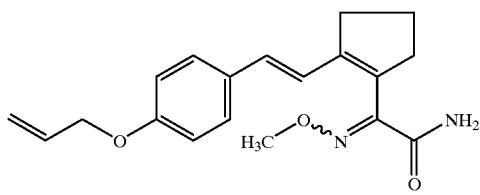

By the method of Example (2), the compound 1-methoxyimino-1-{2-[2-(4-allyl-oxyphenyl)-ethen-1-yl]-penten-1-yl}-acetamide was also prepared by the process c) according to the invention.

$^1$H NMR (CDCl$_3$, TMS): δ=2.0–2.06 (2H); 2.70–2.76 (4H); 4.00 (3H); 4.52–4.55 (2H) ppm.

Preparation of the starting material

Example (IX-1)

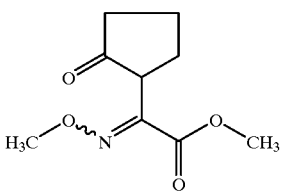

Process d-1)

3 g (17.6 mmol) of 2-methoxalyl-cyclopentanone (M=170.17), 1.5 g (17.95 mmol) of methoxyamine hydrochloride and 2.5 g (18.1 mmol) of potassium carbonate in 17 ml of methanol are heated under reflux for 1 hour. The solvent is distilled off under reduced pressure and the mixture is mixed with water and extracted with dichloromethane. The organic phase is dried over sodium sulphate and concentrated under reduced pressure. The crude product is distilled under reduced pressure. 2.84 g (80.8% of theory) of methyl 1-methoxyimino-1-(2-oxocyclopentan-1-yl) acetate of boiling point 80° C. at 0.4 mb are obtained.

$^1$H NMR (CDCl$_3$, TMS): δ=1.5–2.5 (7H); 3.85 (3H); 4.06 (3H) ppm

Preparation of the starting material

Example (VII-1)

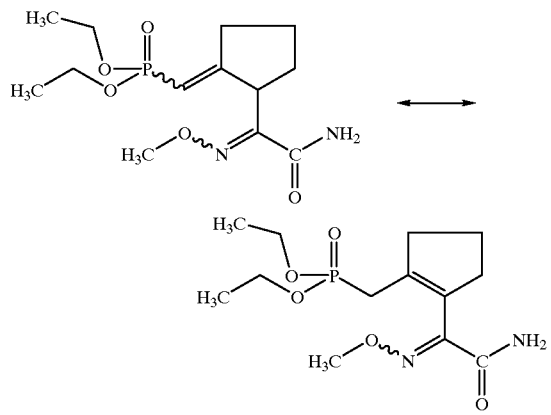

Process c-1a)

9.3 g (0.031 mol) of 1-methoxyimino-1-(2-diethylphosphonomethyl-penten-1-yl)-acetonitrile are stirred with 11.9 g (0.127 mol) of a urea/hydrogen peroxide adduct and 4.2 g (0.031 mol) of potassium carbonate in a mixture of 22 ml of acetone and 22 ml of water at room temperature for 48 hours, an additional 6 g of urea/hydrogen peroxide adduct and 2.1 g of potassium carbonate being added after half the reaction time has passed. The mixture is mixed with water and extracted with ethyl acetate. The organic phase is dried over sodium sulphate and concentrated under reduced pressure. 9.4 g (95.3% of theory) of 1-methoxyimino-1-(2-diethylphosphonomethyl-penten-1-yl)-acetamide are obtained as a mixture of different stereoisomers and tautomers. By GC/MS analysis, the following retention indices and mass fragments are detected (the retention index is based on the n-alkanes C-8–C40, using a capillary quartz column having a poly(methylsiloxane) phase):

| Retention index | M$^+$ |
|---|---|
| 2118 | 319 |
| 2170 | 318 (M-1) |
| 2243 | 319 |

Preparation of the intermediate

Example (XX-1)

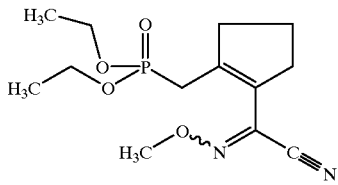

Processes c-2) and c-3)

25.6 g (0.1 mol) of 1-(2-diethylphosphonomethyl-penten-1-yl)-acetonitrile (as a mixture of different stereoisomers and tautomers) and 17.57 g (0.15 mol) of 3-methylbutyl nitrite are dissolved in 50 ml of ethanol and cooled to 0° C. At this temperature, a sodium ethoxide solution, which has been freshly prepared from 2.76 g (0.12 mol) of sodium and 50 ml of ethanol, is added dropwise. The mixture is stirred at 25° C. for 4 hours, 13.86 g (0.11 mol) of dimethyl sulphate are added dropwise, and stirring is continued at 25° C. for a further 18 hours. The mixture is concentrated under reduced pressure, the residue is partitioned between ethyl acetate and water, the organic phase is separated off and dried over sodium sulphate and the solvent is distilled off under reduced pressure. The residue is distilled under reduced pressure. 8 g (26.6% of theory) of 1-methoxyimino-1-(2-diethylphosphonomethyl-penten-1-yl)-acetonitrile of melting point 175° C. at 0.5 mb are obtained.

Preparation of the intermediate

Example (XXI-1)

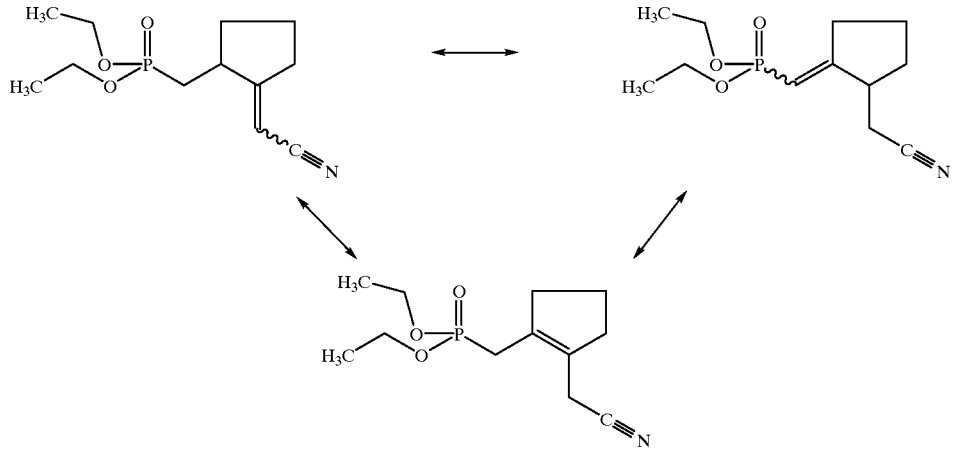

Process c-4)

A mixture of 26.6 g (0.114 mol) of 2-diethylphosphonomethylpentanone (EP-A 453 841), 9.5 g (0.112 mol) of cyanoacetic acid, 1.37 g (0.0228 mol) of acetic acid, 0.88 g (0.0114 mol) of ammonium acetate and 100 ml of toluene is heated under reflux for 3 hours. After cooling, the solution is washed with sodium bicarbonate solution and the organic phase is dried over sodium sulphate and concentrated under reduced pressure. The residue is distilled under reduced pressure. 16 g (54.7% of theory) of 1-(2-diethylphosphonomethyl-penten-1-yl)-acetonitrile of boiling point 150° C. at 0.3 mb are obtained as a mixture of different stereoisomers and tautomers. By GC/MS analysis, the following retention indices and mass fragments are detected (the retention index is based on the n-alkanes C-8–C40, using a capillary quartz column having a poly (methylsiloxane) phase:

| Retention index | M+ |
|---|---|
| 1792 | 259 |
| 1803 | 258 (M-1) |
| 1822 | 259 |
| 1868 | 258 (M-1) |

$^1$H NMR spectrum (CDCl$_3$/TMS): δ=1.25–1.4 (6H); 1.4–2.2 (4H); 2.2–3.3 (6H); 4.0–4.2 (4H) ppm Preparation of the starting material Example (Xa-1)

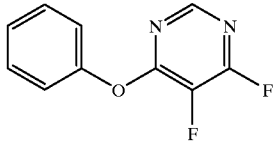

Process d-1b

With stirring, 50.4 g (0.45 mol) of potassium tert-butoxide (M=112.22) are added to a solution of 42.4 g (0.45 mol) of phenol in 400 ml of THF. The resulting potassium phenolate solution is added dropwise to a solution of 80 g (0.6 mol) of 4,5,6-trifluoropyrimidine in 1 l of THF which had been cooled to 0° C., and the mixture is stirred for 30 minutes. The solution is concentrated under reduced pressure and the residue is mixed with water and extracted with ethyl acetate. The organic phase is separated off, dried over sodium sulphate and concentrated under reduced pressure. The crude product is stirred with petroleum ether and filtered off. 63.8 g (68.1% of theory) of 5,6-difluoro-4-phenoxypyrimidine of melting point 65–66° C. are obtained.

Example A

Erysiphe test (wheat)/curative

Solvent: 10 parts by weight of N-methyl-pyrrolidone

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis* f. sp. tritici. 48 hours after the inoculation, the plants are sprayed with the preparation of active compound at the stated application rate.

The plants are placed in a greenhouse at a temperature of about 20° C. and a relative atmospheric humidity of about 80%, in order to promote the development of mildew crystals.

Evaluation is carried out 7 days after the inoculation.

In this test, for example the following compound (1) of the Preparation Examples exhibits, at an active compound application rate of 250 g/ha, an efficacy of 75%.

Example B

*Pseudocercosporella herpotrichoides* test (wheat)/protective

Solvent: 10 parts by weight of N-methyl-pyrrolidone

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the stem bases of the plants are inoculated with spores of *Pseudocercosporella herpotrichoides*.

The plants are placed in a greenhouse at a temperature of about 10° C. and a relative atmospheric humidity of about 80%.

Evaluation is carried out 21 days after the inoculation.

In this test, for example the following compound (1) of the Preparation Examples exhibits, at an active compound application rate of 250 g/ha, an efficacy of 90%.

Example C

Plasmopara test (vines)/protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are inoculated with an aqueous suspension of spores of *Plasmopara viticola* and then are left in a humidity chamber at 20 to 22° C. and 100% relative atmospheric humidity for 1 day. The plants are subsequently placed in a greenhouse at 21° C. and about 90% atmospheric humidity for 5 days. The plants are then moistened and placed in a humidity chamber for 1 day.

Evaluation is carried out 6 days after the inoculation.

In this test, for example the following compounds of the Preparation Examples (1) and (4) exhibit, at an active compound concentration of 100 ppm, an efficacy of 69 to 96%.

We claim:

1. A compound of the formula (I)

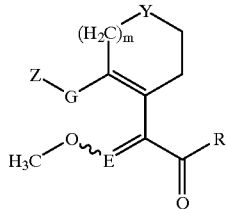

(I)

in which

E represents nitrogen,

G represents a single bond, represents oxygen, sulphur, or represents respectively optionally halogen-, hydroxyl-, alkyl-, halogenoalkyl- or cycloalkyl-substituted alkanediyl or alkynediyl or cycloalkyl-substituted alkenediyl or one of the groupings below —Q—CQ—, —CQ—Q—, —$CH_2$—Q—, —Q—$CH_2$—, —CQ—Q—$CH_2$—, —$CH_2$—Q—CQ—, —Q—CQ—$CH_2$—, —Q—CQ—Q—$CH_2$—, —N=N—, —S(O)$_n$—, —$CH_2$—S(O)$_n$—, —CQ—, —S(O)$_n$—$CH_2$—, —C($R^1$)=N—O—, —C($R^1$)=N—O—$CH_2$—, —N($R^2$)—, —CQ—N($R^2$)—, —N($R^2$)—CQ—, —Q—CQ—N($R^2$)—, —N=C($R^1$)—Q—$CH_2$—, —N($R^2$)—CQ—Q—, —CQ—N($R^2$)—CQ—Q—, —N($R^2$)—CQ—Q—$CH_2$—, —Q—C($R^1$)=N—O—$CH_2$—, —N($R^2$)—C($R^1$)=N—O—$CH_2$—, —O—$CH_2$—C($R^1$)=N—O—$CH_2$—, —N=N—C($R^1$)=N—O—$CH_2$—, —$CH_2$—O—N=C($R^1$)—, —T—$Ar^1$ or —T—$Ar^1$—Q—, where $Ar^1$ represents optionally substituted arylene, heteroarylene, or cycloalkylene or $Ar^1$ represents an aliphatic ring which is doubly attached and in which one or more carbon atoms are replaced by hetero atoms, independently selected from the group consisting of oxygen, sulphur and nitrogen, n represents the number 0, 1 or 2, Q represents oxygen or sulphur, $R^1$ represents hydrogen, cyano or respectively optionally substituted alkyl, alkoxy, alkylthio, alkylamino, dialkylamino or cycloalkyl, and $R^2$ represents hydrogen, hydroxyl, cyano or respectively optionally substituted alkyl, alkoxy or cycloalkyl and T represents a single bond, represents oxygen, sulphur, —$CH_2$—O—, $CH_2$—S— or represents optionally substituted alkanediyl, m represents 0, 1 or 2, R represents alkyl, alkoxy, amino, hydroxylamino, alkoxyamino, alkylamino or dialkylamino, Y represents methylene, and Z represents respectively optionally substituted alkyl, alkenyl, alkynyl, cycloalkyl, aryl or heterocyclyl.

2. A compound of the formula (I) according to claim 1 in which

E represents nitrogen,

G represents a single bond, represents oxygen, sulphur, or represents respectively optionally halogen-, hydroxyl-, $C_1$–$C_4$-alkyl-, $C_1$–$C_4$-halogenoalkyl- or $C_3$–$C_6$-cycloalkyl-substituted alkanediyl or alkynediyl having in each case up to 4 carbon atoms, or alkenediyl having 1 to 3 carbon atoms or one of the groupings below —Q—CQ—, —CQ—Q—, —CH$_2$—Q—, —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^1$)=N—O—, —C(R$^1$)=N—O—CH$_2$—, —N(R$^2$)—, —CQ—N(R$^2$)—, —N(R$^2$)—CQ—, —Q—CQ—N(R$^2$)—, —N=C(R$^1$)—Q—CH$_2$—, —N(R$^2$)—CQ—Q—, —CQ—N(R$^2$)—CQ—Q—, —N(R$^2$)—CQ—Q—CH$_2$—, —Q—C(R$^1$)=N—O—CH$_2$—, —N(R$^2$)—C(R$^1$)=N—O—CH$_2$—, —O—CH$_2$—C(R$^1$)=N—O—CH$_2$—, —N=N—C(R$^1$)=N—O—CH$_2$—, —CH$_2$—O—N=C(R$^1$)—, —T—Ar$^1$ or —T—Ar$^1$—Q—, where n represents the numbers 0, 1 or 2, Q represents oxygen or sulphur, R$^1$ represents hydrogen, cyano, represents respectively optionally halogen-, cyano- or C$_1$–C$_4$-alkoxy-substituted alkyl, alkoxy, alkylthio, alkylamino or dialkylamino having in each case 1 to 6 carbon atoms in the alkyl groups or represents respectively optionally halogen-, cyano-, carboxyl-, C$_1$–C$_4$-alkyl- or C$_1$–C$_4$-alkoxy-carbonyl-substituted cycloalkyl having 3 to 6 carbon atoms, and R$^2$ represents hydrogen, hydroxyl, cyano or represents optionally halogen-, cyano- or C$_1$–C$_4$-alkoxy-substituted alkyl having 1 to 6 carbon atoms or represents optionally halogen-, cyano-, carboxyl-, C$_1$–C$_4$-alkyl- or C$_1$–C$_4$-alkoxy-carbonyl-substituted cycloalkyl having 3 to 6 carbon atoms and Ar$^1$ represents phenylene, naphthylene or cycloalkylene, each of which is optionally mono- or polysubstituted by identical or different substituents, or represents heteroarylene or heterocycloalkylene having 3 to 7 ring members, at least one of which represent oxygen, sulphur or nitrogen and one or two more optionally represent nitrogen, the substituents being selected from the list below:

halogen, cyano, nitro, amino, hydroxyl, formyl, carboxyl, carbamoyl, thiocarbamoyl;

respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 6 carbon atoms in the individual alkyl moieties, and;

cycloalkyl having 3 to 6 carbon atoms and

T represents a single bond, represents oxygen, sulphur, —CH$_2$—O—, CH$_2$—S— or represents alkanediyl having 1 to 3 carbon atoms, m represents 0, 1 or 2, R represents alkyl, alkoxy, amino, alkylamino, hydroxylamino, alkoxyamino or dialkylamino having in each case 1 to 4 carbon atoms, Y represents methylene, and Z represents alkyl having 1 to 8 carbon atoms which is optionally mono- or polysubstituted by identical or different substituents from the group consisting of halogen, cyano, hydroxyl, amino, C$_1$–C$_4$-alkoxy, C$_1$–C$_4$-alkylthio, C$_1$–C$_4$-alkylsulphinyl and C$_1$–C$_4$-alkylsulphonyl (each of which may optionally be substituted by halogen);

represents respectively optionally halogen-substituted alkenyl or alkynyl having in each case up to 8 carbon atoms;

represents cycloalkyl having 3 to 6 carbon atoms which is in each case optionally mono- or polysubstituted by identical or different substituents from the group consisting of halogen, cyano, carboxyl, phenyl (which is optionally substituted by halogen, cyano, C$_1$–C$_4$-alkyl, C$_1$–C$_4$-halogenoalkyl, C$_1$–C$_4$-alkoxy or C$_1$–C$_4$-halogenoalkoxy), C$_1$–C$_4$-alkyl and C$_1$–C$_4$-alkoxycarbonyl;

represents phenyl or naphthyl, each of which is optionally mono- or polysubstituted by identical or different substituents, or represents heterocyclyl having 3 to 7 ring members, at least one of which represents oxygen, sulphur or nitrogen and one or two more optionally represent nitrogen, the substituents being selected from the list below:

halogen, cyano, nitro, amino, hydroxyl, formyl, carboxyl, carbamoyl, thiocarbamoyl;

respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroxyiminoalkyl or alkoxyiminoalkyl having in each case 1 to 6 carbon atoms in the individual alkyl moieties;

alkylene or dioxyalkylene, each of which is doubly attached, each of which has 1 to 6 carbon atoms and each of which is optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

heterocyclyl or heterocyclyl-methyl having in each case 3 to 7 ring members, 1 to 3 of which are in each case identical or different hetero atoms selected from the group consisting of nitrogen, oxygen and sulphur.

3. A compound of the formula (I) according to claim 1 in which

E represents nitrogen,

G represents a single bond, represents oxygen, sulphur or represents respectively optionally fluorine-, chlorine-, bromine-, hydroxyl-, methyl-, ethyl-, n- or i-propyl-, trifluoromethyl-, cyclopropyl-, cyclobutyl-, cyclopentyl- or cyclohexyl-substituted methylene, dimethylene (ethane-1,2-diyl), ethyn-1,2-yl or ethene-1,2-diyl or one of the groupings below —Q—CQ—, —CQ—Q—, —CH$_2$—Q—, —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^1$)=N—O—, —C(R$^1$)=N—O—CH$_2$—, —N(R$^2$)—, —CQ—N(R$^2$)—, —N(R$^2$)—CQ—, —Q—CQ—N(R$^2$)—, —N=C(R$^1$)—Q—CH$_2$—, —N(R$^2$)—CQ—Q—, —CQ—N(R$^2$)—CQ—Q—, —N(R$^2$)—CQ—Q—CH$_2$—, —Q—C(R$^1$)=N—O—CH$_2$—, —N(R$^2$)—C(R$^1$)=N—O—CH$_2$—, —O—CH$_2$—C(R$^1$)=N—O—CH$_2$—, —N=N—(R$^1$)=N—O—CH$_2$—, —CH$_2$—O—N=C(R$^1$)—, —T—Ar$^1$ or —T—Ar$^1$ or —T—Ar$^1$—Q—, where n represents the numbers 0, 1 or 2, Q represents oxygen or sulphur, R$^1$ represents hydrogen, cyano, represents respectively optionally fluorine-, chlorine-, cyano-, methoxy- or ethoxy-substituted methyl, ethyl, n- or i-propyl, n-, i- or s-butyl, methoxy, ethoxy, propoxy, butoxy, methylthio, ethylthio, propylthio, butylthio, methylamino, ethylamino, propylamino, dimethylamino or diethylamino or represents respectively optionally fluorine-, chlorine-, cyano-, carboxyl-, methyl-, ethyl-, n- or i-propyl-, methoxycarbonyl- or ethoxy-carbonyl-substituted cyclopropyl, cyclobutyl, cyclopentyl or cyclohexyl, R$^2$ represents hydrogen, hydroxyl, cyano or represents respectively optionally fluorine-, chlorine-, cyano-, methoxy- or ethoxy-substituted methyl, ethyl, n- or i-propyl, n- or i-, s- or t-butyl or represents respectively optionally fluorine-, chlorine-, cyano-, carboxyl-, methyl-, ethyl-, n- or i-propyl-, methoxy-carbonyl- or ethoxy-carbonyl-substituted cyclopropyl, cyclobutyl, cyclopentyl or cyclohexyl, Ar$^1$ represents respectively optionally mono- to trisubstituted phenylene, naphthylene, furanediyl, thiophenediyl, oxazolediyl, isoxazolediyl, thiazolediyl, isothiazolediyl, 1,2,4-oxadiazolediyl, 1,3,4-oxadiazolediyl, 1,2,4-thiadiazolediyl, 1,3,4-thiadiazolediyl, pyridinediyl, pyrimidinediyl, pyridazinediyl, pyrazinediyl, 1,2,3-triazinediyl, 1,2,4-triazinediyl, 1,3,5-triazinediyl, oxiranediyl, oxetanediyl, tetrahydrofuradiyl, perhydropyranediyl or pyrrolidinediyl, the substituents being selected from the list below:

fluorine, chlorine, methyl, methoxy, methylthio, trifluoromethyl, difluoromethoxy, trifluoromethoxy, difluorochloromethoxy, or cyclopropyl and T represents a single bond, represents oxygen, sulphur, —CH$_2$—O—, CH$_2$—S—, methylene, ethylene or propylene, m represents 0 or 1, R represents methyl, ethyl, n- or i-propyl, methoxy, ethoxy, n- or i-propoxy, amino, methylamino, ethylamino, n- or i-propylamino, hydroxylamino, methoxyamino, dimethylamino, diethylamino, Y represents methylene, and Z represents cyclopropyl, cyclobutyl, cyclopentyl or cyclohexyl, each of which is optionally mono- to hexasubstituted by fluorine, chlorine, bromine, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl, methoxy-carbonyl or ethoxy-carbonyl;

represents respectively optionally mono- to trisubstituted phenyl, naphthyl, furyl, thienyl, oxazolyl, isoxazolyl, thiazolyl, isothiazolyl, 1,2,4-oxadiazolyl, 1,3,4-oxadiazolyl, 1,2,4-thiadiazolyl, 1,3,4-thiadiazolyl, pyridinyl, pyrimidinyl, pyridazinyl, pyrazinyl, 1,2,3-triazinyl, 1,2,4-triazinyl, 1,3,5-triazinyl, oxiranyl, oxetanyl, tetrahydrofuryl, perhydropyranyl, pyrrolidinyl, piperidinyl or morpholinyl, the substituents being selected from the list below:

fluorine, chlorine, bromine, cyano, nitro, amino, hydroxyl, formyl, carboxyl, carbamoyl, thiocarbanoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl or ethoxyiminoethyl; trimethylene (propane-1,3-diyl), methylenedioxy or ethylenedioxy, each of which is doubly attached and each of which is optionally mono- or polysubstituted by identical or different substituents from the group consisting of fluorine, chlorine, methyl, trifluoromethyl, ethyl, n- and i-propyl, cyclopropyl, cyclobutyl, cyclopentyl or cyclohexyl.

4. A compound of the formula (I) according to claim 1, in which

E represents nitrogen,

G represents —O—CH$_2$—, or —CH$_2$—O— and m represents 0 or 1,

R represents methoxy, amino, methylamino or hydroxylamino,

Y represents methylene and

Z represents phenyl which is in each case mono- to trisubstituted by identical or different substituents, the substituents being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoxyiminomethyl, ethoxyiminomethyl, methoxyiminoethyl, ethoxyiminoethyl, methylenedioxy or ethylenedioxy, each of which is doubly attached and each of which is optionally mono- to tetrasubstituted by identical or different substituents from the group consisting of fluorine, chlorine, methyl, trifluoromethyl and ethyl.

5. A compound of the formula (I) according to claim 1 in which

E represents nitrogen,

G represents —C($R^1$)=N—O—CH$_2$—, where
$R^1$ represents hydrogen, cyano, methyl, ethyl or cyclopropyl, m represents 0 or 1, R represents methoxy, amino, methyl amino or hydroxylamino, Y represents methylene and Z represents phenyl, pyridyl or pyrimidinyl, each of which is optionally mono- to trisubstituted by identical or different substituents, the substituents being selected from the list below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoxyiminomethyl, ethoxyiminomethyl, methoxyiminoethyl, ethoxyiminoethyl, or methylenedioxy or ethylenedioxy, each of which is doubly attached and each of which is optionally mono- to tetrasubstituted by identical or different substituents from the group consisting of fluorine, chlorine, methyl, trifluoromethyl or ethyl.

6. A compound of the formula (I) according to claim 1 in which

E represents nitrogen,

G represents —T—Ar$^1$—Q—, where
Q represents oxygen or nitrogen,
Ar$^1$ represents 1,2,4-thiadiazolediyl, 1,3,4-thiadiazolediyl, 1,2,4-oxadiazolediyl, 1,3,4-oxadiazolediyl or represents pyridinediyl, pyrimidinediyl or 1,3,5-triazinediyl, each of which is optionally mono- or disubstituted by identical or different substituents from the group consisting of fluorine, chlorine, cyano, methyl, cyclopropyl, methoxy, methylthio, trifluoromethyl, difluoromethoxy, trifluoromethoxy and difluorochloromethoxy,
T represents a single bond, represents oxygen, sulphur, —CH$_2$—O—, CH$_2$—S—, methylene, ethylene or propylene and m represents 0 or 1, R represents methoxy, amino, methylamino or hydroxylamino, Y represents methylene and Z represents phenyl, pyridyl or thienyl, each of which is optionally mono- to trisubstituted by identical or different substituents from the group consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy, difluorochloromethoxy, trifluoroethoxy, trifluoromethoxy or by methylenedioxy and ethylenedioxy, each of which is doubly attached and each of which is optionally mono- to tetrasubstituted by identical or different substituents from the group consisting of fluorine, chlorine, methyl, trifluoromethyl and ethyl.

7. A compound of the formula (I) according to claim 1 in which

E represents nitrogen,

G represents ethene-1,2-diyl, m represents 0 or 1,

R represents methoxy, amino, methylamino or hydroxylamino,

Y represents methylene and

Z represents phenyl, pyridyl or thienyl, each of which is optionally mono- to trisubstituted by identical or different substituents, the substituents being selected from the list below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoxyiminomethyl, ethoxyiminomethyl, methoxyiminoethyl, ethoxyiminoethyl, methylenedioxy or ethylenedioxy, each of which is doubly attached and each of which is optionally mono- to tetrasubstituted by identical or different substituents from the group consisting of fluorine, chlorine, methyl, trifluoromethyl and ethyl.

8. Process of preparing a compound of the formula (I)

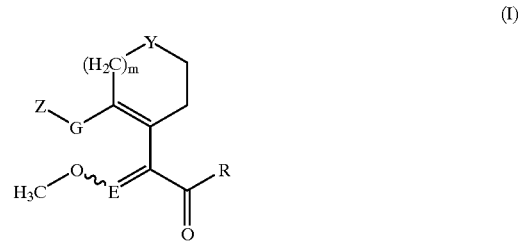

in which

E represents nitrogen,

G represents a single bond, represents oxygen, sulphur, or represents respectively optionally halogen-, hydroxyl-, alkyl-, halogenoalkyl- or cycloalkyl-substituted alkanediyl or alkynediyl or cyclaolkyl-substituted alkenediyl or one of the groupings below —Q—CQ—, —CQ—Q—, —CH$_2$—Q—, —Q—CH$_2$—, —CQ—Q—CH$_2$—, —CH$_2$—Q—CQ—, —O—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C($R^1$)=N—O—, —C($R^1$)=N—O—CH$_2$—, —N($R^2$)—, —CQ—N($R^2$)—, —N($R^2$)—CQ—, —Q—CQ—N($R^2$)—, —N=C($R^1$)—Q—CH$_2$—, —N($R^2$)—CQ—Q—, —CQ—N($R^2$)—CQ—Q—, —N($R^2$)—CQ—Q—CH$_2$—, —Q—C($R^1$)=N—O—CH$_2$—, —N($R^2$)—C($R^1$)=N—O—CH$_2$—, —O—CH$_2$—C(R$^1$)=N—O—CH$_2$—, —N=N—C(R$^1$)=N—O—CH$_2$—, —CH$_2$—O—N=C(R$^1$)—, —T—Ar$^1$ or —T—Ar$^1$—Q—, where Ar$^1$ represents optionally substituted arylene, heteroarylene, or cycloalkylene or Ar$^1$ represents an aliphatic ring which is doubly attached and in which one or more carbon atoms are replaced by hetero atoms, independently selected from the group consisting of oxygen, sulphur and nitrogen, n represents the number 0, 1 or 2, Q represents oxygen or sulphur, R$^1$ represents hydrogen, cyano or respectively optionally substituted alkyl, alkoxy, alkylthio, alkylamino, dialkylamino or cycloalkyl, and R$^2$ represents hydrogen, hydroxyl, cyano or respectively optionally substituted alkyl, alkoxy or cycloalkyl and T represents a single bond, represents oxygen, sulphur, —CH$_2$—O—, CH$_2$—S— or represents optionally substituted alkanediyl, m represents 0, 1 or 2, R represents alkylamino or dialkylamino, Y represents methylene, and Z represents respectively optionally substituted alkyl, alkenyl, alkynyl, cycloalkyl, aryl or heterocyclyl.

comprising reacting an amide of the formula (XIV):

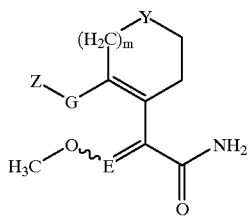

(XIV)

in which

E, G, m, Y and Z are each as defined above, with an alkylating agent of the general formula (XIII)

R$^9$—X$^4$    (XIII)

in which

R$^9$ represents alkyl,

X$^4$ represents halogen or —O—SO$_2$—R$^{10}$ and

R$^{10}$ represents —O—R$^9$, aklyl or optionally substituted aryl, optionally in the presence of a diluent and optionally in the presence of an acid acceptor.

9. The process according to claim 8, wherein said amide of the formula (XIV):

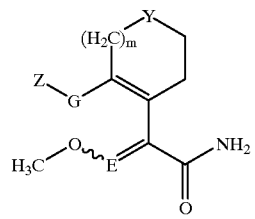

(XIV)

in which

E, G, m, Y and Z are defined as in claim 8, is prepared by a process comprising reacting a phosphorous compound of the formula (VII):

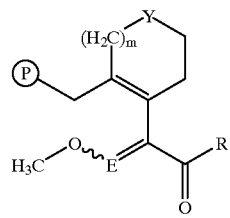

(VII)

in which m, R and Y are each as defined above,

E represents nitrogen,

 represents —P(R$^3$)$_3$+X$^-$ or represents —PO(R$^4$)$_2$,

R$^3$ represents aryl or alkyl

R$^4$ represents alkyl and

X represents halogen, with a keto compound of the general formula (VIII)

$$\underset{Z}{\overset{R^5}{\diagup}}\underset{O}{\diagdown}$$

(VIII)

in which

Z is as defined above and

R$^5$ represents hydrogen, alkyl or cycloalkyl, optionally in the presence of a diluent and optionally in the presence of an acid acceptor.

10. A pesticidal composition comprising a pesticidally effective amount of at least one compound of the formula (I) according to claim 1 and a carrier.

11. Process for preparing a pesticidal composition comprising mixing a pesticidally effective amount of a compound of the formula (I) according to claim 1, with an extender and/or surfactant.

12. A method of controlling pests, comprising applying a pesticidally effective amount of at least one compound of the formula (I) according to claim 1 to the pests, to their habitat or to an area from which it is desired to exclude such pests.

* * * * *